United States Patent [19]

Hahn

[11] Patent Number: 4,816,449

[45] Date of Patent: * Mar. 28, 1989

[54] IMMUNOTHERAPEUTIC ANTI-INFLAMMATORY PEPTIDE AGENTS

[75] Inventor: Gary S. Hahn, Cardiff, Calif.

[73] Assignee: Immunetech Pharmaceuticals, San Diego, Calif.

[*] Notice: The portion of the term of this patent subsequent to Dec. 9, 2003 has been disclaimed.

[21] Appl. No.: 939,927

[22] Filed: Dec. 9, 1986

Related U.S. Application Data

[63] Continuation-in-part of Ser. No. 899,891, Aug. 25, 1986, abandoned, which is a continuation of Ser. No. 824,945, Feb. 3, 1986, Pat. No. 4,628,045, which is a continuation of Ser. No. 746,175, Jun. 18, 1985, abandoned, which is a continuation-in-part of Ser. No. 522,601, Aug. 12, 1983, abandoned.

[51] Int. Cl.$^4$ .................. A61K 37/02; C07K 7/06
[52] U.S. Cl. ..................................... 514/17; 530/330
[58] Field of Search ........................... 530/330; 514/17

[56] References Cited

U.S. PATENT DOCUMENTS

| | | | |
|---|---|---|---|
| 4,161,522 | 7/1979 | Hamburger | 514/17 |
| 4,171,299 | 10/1979 | Hamburger | 530/330 |
| 4,392,997 | 7/1983 | Goldberg | 530/330 |
| 4,628,045 | 12/1986 | Hahn | 530/330 |

OTHER PUBLICATIONS

Ciccimarra, F., et al., PNAS USA, 72(60)2081–2083 (1975).
Dorrington, Keith J., Immunol. Rev., 41:3–25 (1978).
Dreisin, Robert B., et al., New Engl. J. Med., 298(7):353 (1978).
Fantone, Joseph C., et al., AJP, 107(3):397–418 (1982).
Fisher, Alain, et al., J. Immunol., 126(4):1452–1455 (1981).
Goodwin, James S., et al., Clin. Immonol. Immunopath., 15:106–122 (1980).
Goodwin, J. S., et al., Cancer Immunol, Immunother., 8:3–7 (1980).
Hamburger, Robert. N., Science, 189:389–390 (1975).
Hamburger, R. N., Immunol., 38:781 (1979).
Holdsworth, Stephen R., J. Immunol., 130(2):735–739 (1983).
Hunsicker, L. G., et al., J. Exp. Med., 150:413 (1979).
Jasani, B., et al., Biochem. J., 181:623–632 (1979).
Klein, B., et al., J. Immunol, 48:337 (1983).
Kuehl, Frederick A. Jr., et al., Science, 210:978–984 (1980).
Kumar, Pathologic Basis of Disease, Eds. S. L. Robbins & P. S. Cotran, W. B. Saunders; Philadelphia (1979), p. 304.
Lawrence, E. Clinton, et al., New Engl. J. Med., 302(21):1186 (1980).
Leung, Kam H., et al., J. Immunol., 129(4):1742 (1982).
Melewicz, F. M., et al., Clin. Exp. Immunol., 49:364–370 (1982).
Perez, H. Daniel, et al., Textbook Rheumatology, vol. 1, W. B. Saunders, Philadelphia (1982) 179–194.
Perez-Montfort, Ruy, et al., Mol. Immunol., 19(9):1113–1125 (1982).
Plummer, James M., et al., Fed. Proc. 42:713 (1983).
Samuelsson, Bengt, Science, 220:568 (1983).
Spiegelberg, Hans L., Fed. Proc., 42:122 (1983).
Stanworth, D. R., Mol. Immunol., 19(10)1245–1254 (1982).
Stenson, William F., et al., J. Immunol., 125(1):1 (1980).
Striker, Gary E., et al., J. Exp. Med., 149:127–136 (1979).
Takatsu, Kiyoshi, et al., J. Immunol., 114(6):1838 (1975).
Weiss, S. J., et al., J. Immunol., 129(1):309 (1982).
Hunninghake et al. Clin. Immunol Rev. 1(3) 337 (1981–1982).
Johnson et al., (J. Immunol., 117, 1491 (1975).
Boackle et al., (Nature, 282, 742 (1979).
Prystowksy et al. (Biochemistry 20, 6349 (1981).
Lukas et al. (J. Immunol. 127, 2555 (1981).
Burton et al. Nature 288, 338 (1980).
Veretennikova et al. Int. J. Peptide Protein Res., 17, 430 (1981).
Morgan et al. (Proc. Natl. Acad. Sci, USA 79, 5388 (1982).
Ciccimarra et al. (Proc. Natl. Acad. Sci. USA 72 208 (1975).
Stanworth Mol. Immunol. 19 1245 (1982).
Hamburger, Science 189, 389 (1975).
Biochem J., 180 665 (1979).
Barnett-Foster et al. Mol. Immunol 19 407 (1982).
Barnett-Foster et al. J. Immunol 120, 407 (1978).
Fantone, J. Pathol. 107 397 (1982).
Dreisen et al. N. Engl. J. Med. 298 358 (1978).
Lawrence et al. N. Engl. J. Med. 302 1187 (1980).
Spiegelberg, et al., 42, 124 (1983).
Scott et al., Fed. Proc. 42, 129 (1983).

(List continued on next page.)

Primary Examiner—Delbert R. Phillips
Attorney, Agent, or Firm—Lyon & Lyon

[57] ABSTRACT

Anti-inflammatory peptides of the formula A-B-C-D-E, useful in treating allergies, autoimmune diseases, and other disorders, and methods for using them are described.

25 Claims, No Drawings

OTHER PUBLICATIONS

McMillan, N. Engl. J. Med., 304, 1135 (1981).
Fehr et al. (N. Engl. J. Med., 306, 1254 (1982).
Imbach et al. (Lancet, Jun. 6, 1981, p. 1228).
Oberbarnscheidt et al., Immunol., 35, 151 (1978).
Kolsch et al., Immunol. Rev., 49, 61 (1980).
Fridman et al., Immunol Rev. 56, 51 (1981).
Bich-Thuy, J. Immunol., 129, 150 (1982).
Smolen et al., J. Immunol, 129, 10150 (1982).
Goeken et al., Hum. Immunol., 6, 79 (1983).
Kabelitz et al., Eur. J. Immunol., 12, 687 (1982).
Sakane et al., Proc. Natl. Acad. Sci. U.S.A., 75, 3464 (1978).
Miyasaka et al., J. Clin. Invest., 66, 928 (1980).
James et al., J. Clin. Invest., 66, 1305 (1980).
Hodgkin's Lymphoma (Engleman, et al., J. Clin. Invest., 66 149 (1980).
Smith et al., J. Natl. Cancer Inst., 58, 579 (1977).
Cochrane et al., Lancet 1, 441 (1976).
Douvas, Ann. Immunol. Inst. Pasteur, 132C, 307 (1981).
Ulcerative colitis (Hibi, et al., Clin. Exp. Immunol., 49, 75 (1982).
Hashimoto's Thyroiditis (Calder et al., Clin Exp. Immunol., 14, 153 (1973).
Gonzales-Molina et al., J. Clin. Invest., 59, 616 (1977).
Merrifield J. Am. Chem Soc., 85, 2149–2154 (1963).
Barany & Merrifield in the Peptides Eds. E. Gross & F. Meinehofer, vol. 2 (Academic Press, 1980) p. 2 285.
Synthesis of a Tetrapeptide by R. B. Merrifield, Journal of American Chemical Society (vol. 85, pp. 2 2154 (1963).

IMMUNOTHERAPEUTIC ANTI-INFLAMMATORY PEPTIDE AGENTS

This application is a continuation-in-part of application Ser. No. 899,891, filed Aug. 25, 1986, now abandoned, which is a continuation of application Ser. No. 824,945, filed Feb. 3, 1986, now U.S. Pat. No. 4,628,045, which is a continuation of application Ser. No. 746,175, filed June 18, 1985, now abandoned, which is in turn a continuation-in-part of application Ser. No. 522,601, filed Aug. 12, 1983, now abandoned. The instant application also corresponds to Republic of South Africa patent application Ser. No. 84/6192 filed Aug. 9, 1984. The entire specification, drawings, and abstract of all of these applications are incorporated herein by reference.

BACKGROUND OF THE INVENTION

Antibody synthesis is a defense response of higher vertebrates. The molecular entities which stimulate antibody synthesis (e.g., a virus particle) are called antigens. The introduction of an antigen into the body of a higher vertebrate stimulates specific white blood cells, B lymphocytes, to produce antibodies that combine specifically with the antigen to prevent its further multiplication, or to otherwise inactivate it. The study of antibodies and their action with antigens is a branch of immunology.

Antibodies which circulate in blood or other body fluids are termed humoral antibodies, as distinguished from "membrane antibodies" which remain bound to their parent lymphocytes. The term immunoglobulin is used to generically refer to all antibodies. In humans, all immunoglobulins are divided into five classes termed IgG, IgA, IgM, IgD and IgE. Each immunoglobulin molecule consists of two pairs of identical polypeptide chains. The larger pair termed "heavy chains" and designated gamma ($\gamma$), alpha ($\alpha$), mu ($\mu$), delta ($\delta$) and epsilon ($\epsilon$), respectively, are unique for each immunoglobulin class and are linked together by disulfide (S-S) bonds between each chain. Each heavy chain consists of about 400 to 500 amino acid residues linked together by polypeptide bonds. Each light chain, by contrast, consists of about 200 amino acids and are usually linked to a heavy chain by a single disulfide bond.

In 1969, Gerald Edelman first determined the amino acid sequence of an entire human IgG molecule. He found that both heavy and light chains are organized into homology units or "domains" about 100 amino acids in length. Subsequent sequence analysis of the other four immunoglobulin classes demonstrate that they are also organized into structurally similar domains having different amino acid sequences. The first or aminoterminal domain of both light and heavy chains have discrete regions within which considerable variation in amino acids occur. These domains are therefore termed variable (V) domains and are designated $V_H$ in heavy chains and $V_L$ in light chains.

The molecular association of a $V_L$ and $V_H$ domain within an intact immunoglobulin forms an antigen combining site which may bind to a specific antigen with high affinity. The domain structure of all light chains is identical regardless of the associated heavy chain class. Each light chain has two domains, one $V_L$ domain and one domain with a relatively invariant amino acid sequence termed constant, light or $C_L$.

Heavy chains, by contrast may have either three (IgG, IgA, IgD) or four (IgM, IgE) constant or C domains termed $C_H1$, $C_H2$, $C_H3$, and $C_H4$ and one variable domain, termed $V_H$. Alternatively, C domains may be designated according to their heavy chain class; thus $C_\epsilon 4$ indicates the $C_H 4$ domain of the IgE (epsilon) heavy chain.

Visualization of antibodies by electron microscopy or by x-ray diffraction reveals that they have a "Y" shape. IgA and IgM antibodies, in addition, combine in groups of two and five, respectively, to form dimers and pentamers of the basic Y shaped antibody monomer.

When antibodies are exposed to proteolytic enzymes such as papain or pepsin, several major fragments are produced. The fragments which retain antigen binding ability consist of the two "arms" of the antibody's Y configuration and are termed Fab (fragment-antigen binding) or Fab'2 which represent two Fab arms linked by disulfide bonds. The other major fragment produced constitutes the single "tail" or central axis of the Y and is termed Fc (fragment-crystalline) for its propensity to crystallize from solution. The Fc fragment of IgG, IgA, IgM, and IgD consists of dimers of the two carboxy terminal domains of each antibody (i.e., $C_H2$ and $C_H3$ in IgG, IgA, and IgD, and $C_H3$ and $C_H4$ in IgM.) The IgE Fc fragment, by contrast, consists of a dimer of its three carboxy-terminal heavy chain domains ($C_\epsilon 2$, $C_\epsilon 3$ and $C_\epsilon 4$).

The Fc fragment contains the antibody's biologically "active sites" which enable the antibody to "communicate" with other immune system molecules or cells and thereby activate and regulate immune system defensive functions. Such communication occurs when active sites within antibody regions bind to molecules termed Fc receptors.

Fc receptors are molecules which bind with high affinity and specificity to molecular active sites with immunoglobulin Fc regions. Fc receptors may exist as integral membrane proteins within a cell's outer plasma membrane or may exist as free, "soluble" molecules which freely circulate in blood plasma or other body fluids.

Each of the five antibody classes have several types of Fc receptors which specifically bind to Fc regions of a particular class and perform distinct functions. Thus IgE Fc receptors bind with high affinity to only IgE Fc regions or to isolated IgE Fc fragments. It is known that different types of class specific Fc receptors exist which recognize and bind to different locations within the Fc region. For example, certain IgG Fc receptors bind exclusively to the second constant domain of IgG ($C_H2$), while Fc receptors mediating other immune functions bind exclusively to IgG's third constant domain ($C_H3$). Other IgG Fc receptors bind to active sites located in both $C_H2$ and $C_H3$ domains and are unable to bind to a single, isolated domain.

Once activated by antibody Fc region active sites, Fc receptors mediate a variety of important immune killing and regulatory functions. Certain IgG Fc receptors, for example, mediate direct killing of cells to which antibody has bound via its Fab arms (antibody—dependent cell mediate cytotoxicity—(ADCC)). Other IgG Fc receptors, when occupied by IgG, stimulate certain white blood cells to engulf and destroy bacteria, viruses, cancer cells or other entities by a process known as phagocytosis Fc receptors on certain types of white blood cells known as B lymphocytes regulate their growth and development into antibody-secreting plasma cells. Fc receptors for IgE located on certain white cells known as basophils and mast cells, when occupied by antigen bridged IgE, trigger allergic reactions characteristic of hayfever and asthma.

Certain soluble Fc receptors which are part of the blood complement system trigger inflammatory responses able to kill bacteria, viruses and cancer cells. Other Fc receptors stimulate certain white blood cells to secrete powerful regulatory or cytotoxic molecules known generically as lymphokines which aid in immune defense. These are only a few representative examples of the immune activities mediated by antibody Fc receptors.

Most of the amino acids which make up antibodies function as molecular "scaffolding" which determine the antibody's structure, a highly regular three dimensional shape. It is this scaffolding which performs the critical function of properly exposing and spatially positioning antibody active sites which consist of several amino acid clusters. A particular active site, depending upon its function, may already be exposed and, therefore, able to bind to cellular receptors. Alternatively, a particular active site may be hidden until the antibody binds to an antigen, whereupon the scaffolding changes orientation and subsequently exposes the antibody's active site. The exposed active site then binds to its specific Fc receptor located either on a cell's surface or as part of a soluble molecule (e.g., complement) and subsequently triggers a specific immune activity.

Since the function of an antibody's "scaffolding" is to hold and position its acive sites for binding to cells or soluble molecules, the antibody's active sites, when isolated and synthesized as peptides, can perform the immunoregulatory functions of the entire antibody molecule.

Depending upon the particular type of Fc receptor to which an active site peptide binds, the peptide may either stimulate or inhibit immune functions. Stimulation may occur if the Fc receptor is of the type that becomes activated by the act of binding to an Fc region or, alternatively, if an Fc active site peptide stimulates the receptor. The type of stimulation produced may include, but is not limited to, functions directly or indirectly mediated by antibody Fc region-Fc receptor binding. Examples of such functions include, but are not limited to, stimulation of phagocytosis by certain classes of white blood cells (polymorphonuclear neutrophils, monocytes and macrophages); macrophage activation; antibody dependent cell mediated cytotoxicity (ADCC); natural killer (NK) cell activity; growth and development of B and T lymphocytes and secretion by lymphocytes of lymphokines (molecules with killing or immunoregulatory activities).

In 1975, Ciccimarra, et al. (Proc. Natl. Acad. Sci. USA, 72, 2081 (1975)) reported the sequence of a decapeptide from human IgG which could block IgG binding to human monocyte IgG Fc receptors. This peptide is identical to IgG aa 407-416 (Tyr-Ser-Lys-Leu-Thr-Val-Asp-Lys-Ser-Arg). Stanworth, by contrast, was not able to demonstrate that this peptide could block monocyte IgG binding. He did, however, show that the peptide blocked human IgG binding to macrophage IgG Fc receptors of mice (Stanworth, Mol. Immunol., 19, 1245 (1982)).

In 1982, Ratcliffe and Stanworth (Immunol. Lett., 4, 215 (1982)) demonstrated that a peptide identical to IgG aa 295-301 (Gln-Tyr-Asp-Ser-Thr-Tyr-Arg) could slightly block IgG binding to human monocyte IgG Fc receptors. By contrast, a related peptide identical to IgG $C_H2$ residues at aa 289-301 had no monocyte IgG blocking activity.

In 1975, Hamburger reported that a pentapeptide with sequence derived from human IgE $C_\epsilon3$ at aa 320-324 (Asp-Ser-Asp-Pro-Arg) could inhibit a local cutaneous allergic reaction (Prausnitz-Kustner) by approximately 90%. (Hamburger, Science, 189, 389 (1975) and U.S. Pat. Nos. 4,171,299 and 4,161,522.) This peptide, known as the "Human IgE Pentapeptide" (HEPP), has subsequently been shown to inhibit systemic allergic disease in humans after injection by the subcutaneous route. Recent studies demonstrate that the peptide has significant affinity for the IgE Fc receptor of human basophils and can block human IgE binding to basophil IgE Fc receptors by up to 70% (Plummer, et al., Fed. Proc., 42, 713 (1983)). The observed ability of this peptide to block systemic allergic disease in humans is attributed to the peptide's ability to bind to cellular IgE Fc receptors. (Hamburger, Adv. Allergology Immunol. (Pergamon Press: New York, 1980), pp. 591-593).

In 1979 Hamburger reported that a hexapeptide derived from $C_\epsilon4$ at aa 476-481 (Pro-Asp-Ala-Arg-His-Ser) could block human IgE-binding to IgE Fc receptors on a human lymphoblastoid cell line (wil-2wt) (Hamburger, Immunology, 38, 781 (1979)). This peptide had been previously implicated as an agent useful in blocking IgE-binding to human basophil IgE Fc receptors (U.S. Pat. No. 4,161,522).

In 1982, Stanworth (Mol. Immunol., 19, 1245 (1982)) reported that a decapeptide with sequence identical to a portion of $C_\epsilon4$ of human IgE at aa 505-515 (Val-Phe-Ser-Arg-Leu-Glu-Val-Thr-Arg-Ala-Glu) caused a marked enhancement of binding of $^{125}$I-human IgG to mouse macrophages. Interaction of this peptide with Fc receptors, however, was not demonstrated.

In 1979 Stanworth, et al. demonstrated that certain peptides with sequences identical to portions of $C_\epsilon4$ of human IgE, viz. aa 495-506 (Pro-Arg-Lys-Thr-Lys-Gly-Ser-Gly-Phe-Phe-Val-Phe) and smaller derivatives thereof were able to cause degranulation of human and rodent mast cells and thus might be useful in allergic desensitization therapy. (Biochem. J., 180, 665 (1979); Biochem. J., 181, 623 (1979); and European Patent Publication EP No. 0000252). No evidence was presented, however, that these peptides acted by virtue of binding to immunoglobulin Fc receptors.

Past attempts to isolate or synthesize peptides able to block IgE Fc receptors on monocytes/macrophages have uniformly failed. Studies in which IgE was enzymatically degraded or otherwise chemically cleaved and resultant fragments tested for Fc receptor blocking activity demonstrated that no fragment smaller than an intact Fc fragment had measurable IgE Fc receptor interaction. (Takatsu, et al., J. Immunol., 114, 1838 (1975); Dorrington, et al., Immunol. Rev., 41, 3 (1978); Perez-Montfort, et al., Mol. Immunol. 19, 1113 (1982)).

SUMMARY OF THE INVENTION

This invention describes sequences of new and useful peptides that are capable of reducing inflammatory responses associated with autoimmune diseases, allergies and other inflammatory conditions such as those mediated by the mammalian immune system. In particular, it has been discovered that the claimed pentapeptides are useful in blocking inflammation mediated by the arachadonic acid/leukotriene-prostaglandin pathway. Thus, the present peptides may be used effectively in the place of known anti-inflammatory agents, such as steroids, many of which exhibit harmful or toxic side effects. Although these peptides bear a structural similarity to the C$_\epsilon$3 aa 320–324 portion of human IgE, thought to be associated with IgE Fc receptor binding (see discussion above relating to the Human IgE Pentapeptide (HEPP)), it is thought that the present mechanism of anti-inflammatory activity surprisingly does not necessarily involve blocking of Fc receptor binding. Rather, the present peptides have been shown to interact directly in the arachadonic acid-mediated inflammatory pathway and thereby reduce such inflammation. It is believed, however, that the morphological similarities between the present peptides and the IgE molecule may render the claimed peptides useful in regulating immune system-mediated responses, as for example by acting as Fc receptor site blockers.

The claimed peptides have an amino acid sequence A-B-C-D-E, wherein
A is Asp or Glu;
B is Ser, D-Ser, Thr, Ala, Gly or Sarcosine;
C is Asp, Glu, Asn or Gln;
D is Pro, Val, Ala, Leu or Ile; and
E is Arg, Lys or Orn.
Pharmaceutically acceptable salts of these peptides, as well as derivatives including amino-terminal N-acetyl derivatives, are also included within the scope of the present invention.

DETAILED DESCRIPTION OF THE INVENTION

The present invention describes new peptides and therapeutic compositions that are useful in reducing inflammation associated with a variety of human disease conditions including allergies (including true IgE-mediated allergic responses), non-IgE-mediated inflammatory responses such as those associated with chronic refractory idiopathic urticharia and giant papillary conjunctivitis, autoimmune diseases and other inflammatory conditions. The effectiveness of the peptides is thought to be due, at least in part, to their ability partially or wholly to block the arachadonic acid-mediated inflammation pathway that is involved, to a greater or lesser extent, in all known inflammation conditions. As is well known, this pathway generates exceedingly potent substances, including the leukotrienes and prostaglandins, responsible for the inflammatory response.

The present peptides are also thought to be useful in blocking the binding of IgG and IgE immunoglobulins to Fc receptors on monocytes and macrophages (MMs), basophils, and other cells or receptors involved in the immune system and inflammatory resposses.

Thus, an important object of the present invention is to describe how such new and useful peptides and their analogs and derivatives may be used to treat certain human diseases in which molecular elements, cellular elements or immune complexes contribute to disease pathogenesis. Such diseases include, but are not limited to, rheumatoid arthritis, systemic lupus erythematosus, glomerulonephritis, serum sickness, polyarteritis nodosa and other forms of vasculitis, and other diseases described under the generic category of "autoimmune diseases", idiopathic pulmonary fibrosis, hypersensitivity pneumonitis, asthma, chronic refractory urticharia, giant papillary conjunctivitis and other diseases and conditions.

Other objects and advantages of the invention will be apparent to those in the art from the preceding and following description of the invention.

In the following sections, the amino acid components of the peptides are identified as abbreviations for convenience. Thes abbreviations are intended to include both the D- and L-forms although the L- form is preferred:

| Amino Acid | Abbreviation |
|---|---|
| glycine | GLY |
| L-alanine | ALA |
| L-valine | VAL |
| L-leucine | LEU |
| L-isoleucine | ILE |
| L-proline | PRO |
| L-methionine | MET |
| L-cysteine | CYS |
| L-phenylalanine | PHE |
| L-tyrosine | TYR |
| L-tryptophan | TRP |
| L-histidine | HIS |
| L-lysine | LYS |
| L-arginine | ARG |
| L-aspartic acid | ASP |
| L-asparagine | ASN |
| L-glutamic acid | GLU |
| L-glutamine | GLN |
| L-serine | SER |
| L-threonine | THR |
| L-ornithine | ORN |
| sarcosine | SAR |

Carbobenzoxyl amino acid
N—acetyl amino acid
des-αamino amino acid
Z - amino acid
Ac - amino acid
desamino-amino acid

The Mammalian Inflammatory Response

It is generally recognized that PMNs and MMs (mnnocytes are immature macrophages) accumulate in great numbers at the sites of most acute immunologically induced tissue injury. It has been recently appreciated that these cells are not mere passive "bystanders" in the inflammatory process, but rather directly contribute to tissue inflammation and destruction. PMNs and monocytes contain cellular organelles known as lysosomes which contain proteolytic enzymes and inflammatory mediators sequestered in a latent, inactive form. Under certain conditions, PMNs and MMs are stimulated to release the contents of their lysosomes to the external cellular millieu, resulting in considerable tissue inflammation and cell death. Such inflammation and cell death are mediated by a variety of biologically active substances. The lysosomal granules of PMNs and MMs contain many different proteolytic and glycolytic enzymes (viz. collagenase which degrades collagen, elastase which degrades elastin, lysozyme which degrades certain types of carbohydrate polymers, etc.) which cause direct destruction of cartilage, connective tissue and cells. Certain of these enzymes may also activate the blood clotting system or inflammatory peptide mediators such as bradykinin or complement. Other important inflammatory mediators released by PMNs and MMs include prostaglandins (PGs) and leukotrienes (LTs) which have a variety of potent inflammatory and immunomodulatory effects. Some of these effects, together with the eliciting substance are enumerated below.

(1) Prostaglandin E2 (PGE2)--PGE2 produces vasodilation, erythema, increased vascular permeability, edema (swelling), potentiates the inflammatory and pain producing actions of histamine and bradykinin and stimulates bacterial endotoxin induced collagenase production by leukocyte (Kuehl, et al., Science, 210, 978 (1980)).

PGE2 also has potent immunosuppressive effects and can suppress NK and ADCC-mediated killing of cancer cells, T cell colony growth, clonal proliferation of the committed granulocyte macrophage stem cell and antigen and mitogen-induced B-lymphocyte maturation into antibody-secreting plasma cells. PGE2 also directly activates short-lived T suppressor lymphocytes which can, in turn, suppress other protective immune functions. Such PGE2-mediated suppression of the immune system is thought to be important in producing the immunosuppression that frequently accompanies various forms of cancer. (Goodwin, Clin. Immunol. Immunopath., 15, 106 (1980); Stenson, et al., Immunol. 125, 1 (1980); Oroller, et al., Cell. Immunol., 39, 165 (1978); Leung, et al., J. Immunol., 129, 1742 (1982); Fischer, et al., J. Immunol., 126, 1452 (1981); Klein, et al., Immunol., 48, 337 (1983); Goodwin, et al., Cancer Immunol. Immunother., 8, 3 (1980)).

(2) Leukotrienes C4 (LTC4), D4 (LTD4) and E4 (LTE4) These leukotrienes, in various combinations, constitute the slow reacting substance of anaphylaxis (SRS A) thought to be important in the pathogenesis of many inflammatory and allergic diseases, especially asthma. These leukotrienes are hundreds to thousands of times more potent, on a molar basis, than histamine in eliciting inflammation and pulmonary bronchoconstriction. (Samuelsson, Science, 220, 568 (1983)).

(3) Leukotriene B4 (LTB4) This leukotriene is one of the most potent chemotatic substances known for certain human leukocytes. It is produced by preparations of human peripheral leukocytes, neutrophils, lung tissue and other cells. LTB4 attracts neutrophils, and eosinophils, both of which are present in high numbers at sites of inflammation.

LTB4 also stimulates the release of lysosomal enzymes, including lysozyme, from neutrophils which directly mediates tissue destruction. LTB4 is probably involved in the pathogenesis of many inflammatory conditions, including rheumatoid arthritis in which LTB4 is found in elevated concentrations in affected joints. (Samuelsson, Science, 220, 568 (1983); Science, 215, 1382 (1982)).

Immune complexes also cause PMNs and MMs to release highly reactive free radicals such as the superoxide anion ($O_2$) which directly damages tissue which it contacts. (Weiss, et al., J. Immunol., 129, 309 (1982); Fantone, J. Pathol, 107, 397 (1982)).

Of central importance to the present invention is the ability of the claimed peptides to reduce substantially the inflammatory response associated with leukotrienes, prostaglandins and other substances generated in the course of the well-known arachidonic acid pathway. This pathway is implicated to some degree in all known inflammatory responses in humans, including the allergic response. As is discussed below, inhibition of up to 70% has been observed in in vivo bioassays using the arachidonic acid-induced ear edema model of inflammation in mice. Certain of the peptides tested exceed the inhibitory capability of HEPP, the Human IgE pentapeptide, discussed above, which is known to be useful in reducing the allergic response.

Also of importance to this invention is the fact that IgG and IgE-containing immune complexes, aggregates or objects to which IgG or IgE is attached via Fab mediated binding or by passive surface adsorption ("complexes") are potent stimulators of phagocytosis (engulfment and digestion of complexes, particulate matter and cells) by PMNs and MMs and subsequent enzyme and inflammatory mediator release. Such stimulation is known to depend on the binding of IgG or IgE Fc regions within immune complexes to Fc receptors located on the PMN or MM cell surface.

It is known that the exact molecular form in which Fc regions are presented to PMN Fc receptors (e.g., IgG or IgE antigen complexes, heat aggregated IgG or IgE, IgG or IgE passively adsorbed to cell or particulate surfaces) is not important in triggering lysosomal enzyme or inflammatory mediator release. The critical factor in common to these stimulatory forms of IgG or IgE is that multiple Fc regions in a fixed, relatively immobilized form be present to simultaneously bind to multiple PMN or MM Fc receptors. Such multiply-engaged Fc receptors then trigger lysosomal enzyme or inflammatory mediator release. The ability of the present peptides to block such binding may prove useful in regulating inflammatory responses mediated by immune complexes.

Basophils are members of the granulocytic series of blood leukocytes. Together with their tissue analogs, mast cells, basophils contain the majority of the body's histamine which may be released during allergic reactions or other conditions. Although basophils and mast cells are morphologically and developmentally distinct, their manner of participation in the human allergic response appears to be similar. In both basophils and mast cells, histamine and other vasoactive and inflammatory substances are contained within multiple cytoplasmic granules which upon staining appear dark blue-black. Both cell types also have similar, if not identical, Fc receptors for IgE on their cellular surface. These receptors are normally partially occupied by circulating IgE which is bound to the receptor via active sites in the Fc region. When a polyvalent antigen simultaneously binds to two adjacent Fc receptor-bound IgE molecules causing them to be "bridged," a rapid series of biochemical events occur resulting in granule exocytosis and release of inflammatory substances including histamine, leukotrienes, platelet activating factor, eosinophil chemotactic factors and a variety of other substances. Such IgE-mediated basophil and mast cell degranulation is thought to directly produce most of the signs and symptoms of human allergic diseases including extrinsic asthma, allergic rhinoconjunctivitis ("hay fever"), allergic eczema and allergic reactions to insect bites and foods.

The peptides described in this invention have antiallergic activities, in addition to the effects previously described. It is known that IgE-mediated allergies, viz. allergic rhinitis (hayfever), types of asthma, and allergic reactions to insect stings, occur by a mechanism in which IgE is bound, via its Fc region, to IgE Fc receptors located on mast cells and basophils. When the offending allergen (the antigen which originally elicited IgE synthesis) is presented to such sensitized mast cells and basophils and binds to the cell-bound IgE, inflammatory mediators are released which produce the immediate allergic reaction characteristic of allergies. If the sensitizing IgE is prevented from binding to mast cell or basophil IgE Fc receptors, however, mediator release does not occur. It is known that mast cell and basophil IgE Fc receptors may be blocked by administering either chemically isolated IgE Fc fragments or certain peptides that are described in the United States and foreign patents discussed above. Such compounds have affinity for the IgE Fc receptor and thus bind to it and prevent IgE from binding. In this manner, the allergic response can be abrogated independent of the particular antigen which elicited IgE synthesis. (Hamburger, Science, 189, 389 (1975); Hamburger, Adv. Allergology Immunol. (Pergamon Press: New York, 1980), pp. 591-593; Plummer, et al., Fed. Proc., 42, 713 (1983)).

It is believed that the peptides described in the present invention can bind to IgE Fc receptors on human basophils and can block subsequent IgE binding. These peptides therefore have antiallergic properties which may be useful in the treatment of allergy in animals and in humans. In addition, the peptides may be used to reduce the inflammatory effects of basophilrelated or mast cell-related allergic responses by blocking the action of the arachadonic acid pathway, as discussed above.

EXAMPLES OF DISEASE PROCESSES IN WHICH IMMUNE COMPLEX MEDIATED LYSOSOMAL ENZYME OR INFLAMMATORY MEDIATOR RELEASE CONTRIBUTE TO INFLAMMATION AND TISSUE DESTRUCTION

I. Rheumatoid Arthritis (RA)

Lesions of RA are thought to first develop within joint spaces. An as yet unidentified agent or condition triggers a local, intraarticular synthesis of IgG and IgM antibodies directed toward the Fc region of IgG. Such "rheumatoid factors (RFs)", being a type of immune complex, accumulate within the joint and bind to Fc receptors of leukocytes, including PMNs and of the complement system. Such binding triggers an initial inflammatory reaction which attracts blood-borne leukocytes, especially PMNs. PMNs in large numbers migrate into the joint space and, there, encounter RF immune complexes which trigger lysosomal enzyme secretion and subsequent cartilage and tissue destruction. While other leukocytes including monocytes and macrophages also contribute to the inflammation by a similar process, PMNs frequently constitute the great majority of cells present and often exceed 25,000 PMNs per cubic millimeter. RFs also activate the complement system which, in conjunction with PMNs and other cells and molecules, produce the tissue destruction characteristic of the disease. (Perez, et al. in Textbook of Rheumatology, Vol. 1 (W. B. Saunders: Philadelphia, 1981), pp. 179-194). It is believed that the peptides detailed in the present invention can block IgG immune complex binding to PMNs, monocytes and macrophages and can thereby reduce or prevent inflammation and tissue destruction of rheumatoid arthritis and other immune complex-mediated inflammation. Moreover, the ability of the peptides to block the arachadonic acid-induced inflammatory response associated with these diseases represents a separate mechanism for therapeutic utility.

II. Idiopathic Pulmonary Fibrosis

Idiopathic Pulmonary Fibrosis (IPF) is a condition in which the normally thin, gas permeable wall of the lung's respiratory unit, the alveolus, is greatly thickened and replaced with large amounts of relatively gas impermeable, fibrous connective tissue. This greatly reduces the lung's ability to respire and may lead to chronic pulmonary incapacitation and death. IPF frequently accompanies idiopathic interstitial pneumonias and the interstitial pneumonias of rheumatoid arthritis, systemic lupus erythematosus, scleroderma and polymyositis dermatomyositis. (Dreisin, et al., N. Engl. J. Med. 298, 353 (1978)). The final common pathway leading to the tissue destruction in IPF is believed to involve IgG-immune complexes produced either systemically or locally within the lung parenchyma. (Lawrence, et al., N. Engl. J. Med. 302, 1187 (1980)). Localization of immune complexes within the lung leads to an influx of PMNs and monocytes from blood which accumulate in large numbers within the interstitium and within alveolar structures. Monocytes then develop into mature macrophages and join the normally present pulmonary macrophages. IgG Fc regions within the immune complexes then combine with PMN and MM Fc receptors causing lysosomal enzyme and inflammatory mediator release, inflammation and alveolar destruction. (Hunninghake, et al., Clin. Immunol. Rev., 1(3), 337 (1981-1982)). Over a period of time, this process results in "scarring" and generalized pulmonary fibrosis. It is believed that the peptides detailed in the present invention can block IgG immune complex binding to IgG Fc receptors on PMNs, monocytes and macrophages and can thereby reduce or prevent inflammation and tissue destruction of idiopathic pulmonary fibrosis and other immune complex mediated diseases. Moreover, the ability of the peptides to block the arachadonic acid-induced inflammatory response associated with these diseases represents a separate mechanism for therapeutic utility.

III. Immune Complex Induced Glomerulonephritis

The glomeruli of kidneys are the filtration devices which separate from blood the plasma ultra-filtrate that ultimately becomes urine. Glomeruli are easily damaged by the inflammatory processes initiated by immune complexes which accumulate as a result of the blood filtration process. At an early stage of immune complex-induced glomerular injury, monocytes and macrophages accumulate in the glomerular mesangium where they encounter immune complexes. IgG Fc regions within these complexes bind to IgG Fc receptors of the monocytes and macrophages and are thereby stimulated to release lysosomal enzymes and the inflammatory mediators previously discussed. These substances produce glomerular inflammation, (glomerulonephritis) which may lead to kidney failure and subsequent death. (Holdsworth, J. Immunol., 130, 735 (1983); Striker, J. Exp. Med. 149, 127 (1979); Hunsicker, J. Exp. Med., 150, 413 (1979)). Immune complex-mediated glomerulonephritis and resultant kidney failure, for example, is the single leading cause of death in patients with systemic lupus erythematosis. (Kumar in Pathologic Basis of Disease, eds. S. L. Robbins and R. S. Cotran (W. B. Saunders; Philadelphia, 1979), p. 304). Many other conditions such as rheumatoid arthritis, other autoimmune diseases, infectious diseases such as streptococcus or hepatitis virus infection and others are accompanied by glomerulonephritis caused by immune complexes. It is believed that the peptides detailed in the present invention can block IgG immune complex binding to monocyte and macrophage IgG Fc receptors and can thereby reduce or prevent inflammation and tissue destruction of immune complex-mediated glomerulonephritis. Moreover, the ability of the peptides to block the arachadonic acid-induced inflammatory response associated with these diseases represents a separate mechanism for therapeutic utility.

IV. Immune Complex Mediated Lung-Inflammation of Hypersensitivity Pneumonitis Hypersensitivity Pneumonitis (HP) includes a spectrum of conditions characterized by granulomatous interstitial and alveolar-filling lung diseases associated with exposure to a wide range of inhaled organic dusts and particles. Affected individuals synthesize relatively large amounts of IgG directed against the offending inhaled dust and produce IgG immune complexes within the lung parenchyma. These complexes bind to IgG Fc receptors of PMNs, monocytes and pulmonary macrophages which, in a manner similar to that previously discussed, are stimulated to release lysosomal enzymes and inflammatory mediators which produce an acute pneumonia. If this process is continued for a period of time, the lung damage may become permanent in the form of chronic granulomatous interstitial pneumonitis. (Stankus, Allergologie, 4, 8 (1981)). It is believed that the peptides detailed in the present invention can block IgG-immune complex binding to IgG Fc receptors of PMNs, monocytes and macrophages and can thereby reduce or prevent inflammation and tissue destruction of hypersensitivity pneumonitis and other immune-complex mediated diseases. Moreover, the ability of the peptides to block the arachadonic acid-induced inflammatory response associated with these diseases represents a separate mechanism for therapeutic utility.

V. IgE Immune Complex Mediated Inflammation in Asthma

Atopic (IgE-mediated) asthma is an inflammatory lung disease in which IgE bound to pulmonary mast cells and circulating basophil Fc receptors causes them to release inflammatory mediators upon exposure to the sensitizing allergan (antigen). It is also known that IgE not already bound to cellular Fc receptors may also bind to the sensitizing allergan to form IgEallergan immune complexes. These circulating IgE immune complexes may then bind to monocyte or macrophage IgE Fc receptors causing them to release the various inflammatory mediators previously discussed. Additionally, IgG directed against the sensitizing allergan may be present and may also produce IgG-allergan immune complexes. These complexes may then bind to IgG Fc receptors on PMNs and monocytes and macrophages in the lungs and thereby contribute to lysosomal enzyme and inflammatory mediator release. It is believed that the peptides detailed in the present invention can block IgE immune complex binding to IgE Fc receptors on monocytes and macrophages and can thereby reduce or prevent inflammation characteristic of asthma and other disease pathogenesis. (Melewicz, et al., Clin. Exp. Immunol., 49, 364 (1982); Spiegelberg, et al., 42, 124 (1983); Scott, et al., Fed. Proc., 42, 129 (1983)). Moreover, the ability of the peptides to block the arachadonic acid-induced inflammatory response associated with these diseases represents a separate mechanism for therapeutic utility.

Peptides which block immune complex binding to Fc receptors may also be xpected to stimulate cellular or delayed type hypersensitivity (DTH) which is known to be important in defense against cancer and certain infectious diseases such as tuberculosis. Immune complexes can significantly inhibit DTH in experiments using mice (Douvas, Ann. Immunol. Inst. Pasteur, 132C, 307 (1981)). Such inhibition is known to be dependent on the presence of Fc regions within the immune complex which bind to cellular Fc receptors.

Other diseases which may usefully be treated using the peptides of the present invention include autoimmune hemolytic anemias, idiopathic (autoimmune) thrombocytopenic purpura (ITP), Sjogren's syndrome, primary biliary cirrhosis, Hodgkin's lymphoma, chronic lymphocytic leukemia, diseases involving improper ADCC-mediated cell killing, certain types of kidney diseases, inflammatory bowel diseases such as ulcerative colitis and regional enteritis (Crohn's disease), hypersensitivity pneumonitis, certain types demyelinating neurologic diseases such as multiple sclerosis, certain types of endocrinological diseases such as Grave's disease or Hashimoto's thyroiditis, certain types of cardiac diseases such as rheumatic fever, diseases involving diminished or increased T- or B-lymphocyte development, including AIDS, diseases involving improper antibody synthesis as regulated by immunoglobulin-binding factors (IBF's), and diseases involving improper peptide modulation by the T-cell Replacing Factor (TRF).

ANTI-INFLAMMATORY PEPTIDES OF THE PRESENT INVENTION

As indicated above, this invention is concerned with a method of blocking immune-complex-mediated inflammation, new peptides having therapeutic value in various areas, therapeutic compositions containing these peptides, and methods for use thereof.

The peptides of the present invention are described by the formula A-B-C-D-E wherein:

A is Asp or Glu;
B is Ser, D-Ser, Thr, Ala, Gly or Sar;
C is Asp, Glu, Asn or Gln;
D is Pro, Val, Ala, Leu or Ile; and
E is Arg, Lys or Orn, including pharmaceutically acceptable salts and other chemical derivatives of these peptides. Excluded from the scope of the invention are the peptides Asp-Ser-Asp-Pro-Arg, Asp-Ser-Asn-Pro-Arg and Asp-Thr-Glu-Ala-Arg. Shorter sequences within the above pentapeptide, such as those disclosed herein, may also yield effective anti-inflammatory compounds.

Particularly suitable chemical derivatives of the present peptides are the amino-terminal N-acetyl derivatives. Other suitable derivatives include des-alpha-amino peptides, and N-alpha acyl substituents of the form RCO—, where R is preferably an unbranched or branched lower alkyl group of from one to eight carbons, or may be alkenyl, alkynyl, aryl, alkaryl, aralkyl or cycloalkyl. Such amino-terminal substituents may increase activity by preventing or slowing the course of enzymatic degradation of the peptides in the in vivo environment. (The use of D-enantiomeric amino acids, as for example D-Ser in position B, will also typically prevent or slow enzymatic degradation.) Carboxyl-terminal substituents, such as those of the form —NHR, where R is hydrogen or a lower (one to eight carbon) alkyl, are also preferred derivatives of the present peptides. R may also be alkenyl, alkynyl, aryl, alkaryl, aralkyl or cycloalkyl. Secondary amino groups of the form —NR$_2$ may also yield active peptides amides.

Preferred sequences are as follows:
Glu-Ser-Asp-Pro-Arg,
Asp-Thr-Asp-Pro-Arg,
Glu-Thr-Asp-Pro-Arg,
Asp-Ala-Asp-Pro-Arg, Glu-Ala-Asp-Pro-Arg,
Glu-Ser-Glu-Pro-Arg,
Asp-Thr-Glu-Pro-Arg,
Glu-Thr-Glu-Pro-Arg,
Asp-Ala-Glu-Pro-Arg,
Glu-Ala-Glu-Pro-Arg,
Asp-Ser-Asp-Val-Arg,
Glu-Ser-Asp-Val-Arg,
Asp-Thr-Asp-Val-Arg,
Glu-Thr-Asp-Val-Arg,
Asp-Ala-Asp-Val-Arg,
Glu-Ala-Asp-Val-Arg,
Asp-Ser-Glu-Val-Arg,
Glu-Ser-Glu-Val-Arg,
Asp-Thr-Glu-Val-Arg,
Glu-Thr-Glu-Val-Arg,
Asp-Ala-Glu-Val-Arg,
Glu-Ala-Glu-Val-Arg,
Asp-Ser-Asp-Ala-Arg,
Glu-Ser-Asp-Ala-Arg,
Asp-Thr-Asp-Ala-Arg,
Glu-Thr-Asp-Ala-Arg,
Asp-Ala-Asp-Ala-Arg,
Glu-Ala-Asp-Ala-Arg,
Asp-Ser-Glu-Ala-Arg,
Glu-Ser-Glu-Ala-Arg,
Asp-Thr-Glu-Ala-Arg,
Glu-Thr-Glu-Ala-Arg,
Asp-Ala-Glu-Ala-Arg,
Glu-Ala-Glu-Ala-Arg,
Asp-Ser-Asp-Pro-Lys,
Glu-Ser-Asp-Pro-Lys,
Asp-Thr-Asp-Pro-Lys,
Glu-Thr-Asp-Pro-Lys,
Asp-Ala-Asp-Pro-Lys,
Glu-Ala-Asp-Pro-Lys,
Asp-Ser-Glu-Pro-Lys,
Glu-Ser-Glu-Pro-Lys,
Asp-Thr-Glu-Pro-Lys,
Glu-Thr-Glu-Pro-Lys,
Asp-Ala-Glu-Pro-Lys,
Glu-Ala-Glu-Pro-Lys,
Asp-Ser-Asp-Val-Lys,
Glu-Ser-Asp-Val-Lys,
Asp-Thr-Asp-Val-Lys,
Glu-Thr-Asp-Val-Lys,
Asp-Ala-Asp-Val-Lys,
Glu-Ala-Asp-Val-Lys,
Asp-Ser-Glu-Val-Lys,
Glu-Ser-Glu-Val-Lys,
Asp-Thr-Glu-Val-Lys,
Glu-Thr-Glu-Val-Lys,
Asp-Ala-Glu-Val-Lys,
Glu-Ala-Glu-Val-Lys,
Asp-Ser-Asp-Ala-Lys,
Glu-Ser-Asp-Ala-Lys,
Asp-Thr-Asp-Ala-Lys,
Glu-Thr-Asp-Ala-Lys,
Asp-Ala-Asp-Ala-Lys,
Glu-Ala-Asp-Ala-Lys,
Asp-Ser-Glu-Ala-Lys,
Glu-Ser-Glu-Ala-Lys,
Asp-Thr-Glu-Ala-Lys,
Glu-Thr-Glu-Ala-Lys,
Asp-Ala-Glu-Ala-Lys,
Glu-Ala-Glu-Ala-Lys,
Asp-D-Ser-Asp-Pro-Arg,
Glu-D-Ser-Asp-Pro-Arg,
Asp-D-Ser-Glu-Pro-Arg,
Glu-D-Ser-Glu-Pro-Arg,
Asp-D-Ser-Asp-Val-Arg,
Glu-D-Ser-Asp-Val-Arg,
Asp-D-Ser-Glu-Val-Arg,
Glu-D-Ser-Glu-Val-Arg,
Asp-D-Ser-Asp-Ala-Arg,
Glu-D-Ser-Asp-Ala-Arg,
Asp-D-Ser-Glu-Ala-Arg,
Glu-D-Ser-Glu-Ala-Arg,
Asp-D-Ser-Asp-Pro-Lys,
Glu-D-Ser-Asp-Pro-Lys,
Asp-D-Ser-Glu-Pro-Lys,
Glu-D-Ser-Glu-Pro-Lys,
Asp-D-Ser-Asp-Val-Lys,
Glu-D-Ser-Asp-Val-Lys,
Asp-D-Ser-Glu-Val-Lys,
Glu-D-Ser-Glu-Val-Lys,
Asp-D-Ser-Asp-Ala-Lys,
Glu-D-Ser-Asp-Ala-Lys,
Asp-D-Ser-Glu-Ala-Lys,
Glu-D-Ser-Glu-Ala-Lys, It is to be considered that the scope of the present invention is inclusive of the unsubstituted peptides as well as those which are terminally substituted by one or more functional groups which do not substantially affect the biological activity disclosed herein. From this statement it will be understood that these functional groups include such substituents as acylation on the free amino group and amidation on the free carboxylic acid group, as well as the substitution of the D-isomers of amino acids in place of the naturally occurring L-isomers. It is also envisioned that certain amino acids within an active site peptide may be substituted with amino acids which are chemically similar by virtue of similar side chain size, charge, shape, solubility, and other chemical characteristics while retaining the peptide's biological activity. Amino acids with such chemical similarity are termed "functionally conserved."

Possible "functionally" conserved amino acids which could be used for substitution do not necessarily need to be selected from the twenty naturally-occurring amino acids. Other amino acids having chemical properties similar to one of the specified eight groups may also be used as substituents in a particular class, for example, ornithine or homoarginine have basic side chains similar to Lys, Arg and His and may thus be effectively substituted for Lys, Arg or His. For example, both Lys and Arg have been shown to be active in the E-position of the peptide. It is expected that anti-inflammatory peptides of the present invention may also have functionally conserved amino acids substituted for one or more of their amino acids while maintaining or even increasing biological activity.

As one example of the biological effectiveness of the peptides of the present invention, the peptides have been shown to be effective in reducing inflammatory responses as reflected in the arachadonic acid-induced ear edema model of inflammation. This assay is known to be relevant to the human allergic response, and demonstrates inhibitory activity of the claimed peptides as well as of HEPP (Asp-Ser-AspPro-Arg), a pentapeptide with known anti-allergic effects.

In the arachadonic acid-induced ear edema model of inflammation, both classes of eicosanoids, prostaglandins and leukotrienes, are detected and their appearance preceeds both the edematous and cellular infiltrative phases. Leukotriene (LT)$C_4$ and $LTD_4$ enhance vascular permeability and may be involved in the edematous phase of an inflammatory reaction. In addition, $LTC_4$, $LTD_4$ and $LTE_4$ have been shown to be equivalent to the classical slow reacting substance of anaphylaxis (SRS-A) which functions as a primary spasmogen in asthma. The cyclooxygenase product prostaglandin $(PG)E_2$ is a vasodilator and serves to exacerbate the vascular permeability change induced by other mediators. Prostaglandin $D_2$ is thought, for example, to be a major mediator in allergic rhinitis. The cellular component of inflammation is mediated by a number of factors including $LTB_4$. See Movat, *The Inflammatory Reaction*, pp. 77–159 (Elsevier Science Publishing Co., Inc. 1985).

The arachadonic acid-induced ear edema assay is a modification of the procedure described by Young et al., *J. Inv. Derm.* 80, 48–52 (1983). Peptides to be tested were injected subcutaneously at the base of the neck of female SJL/J mice (23-27 g) 1 hour prior to the ear edema assay. Five animals were used per group. The peptides were each dissolved in phosphate buffered saline at a concentration 25 mg/ml and 0.100 ml was injected per mouse. Arachadonic acid, greater than 99% pure (Behring Diagnostics), was dissolved in acetone as a vehicle. Ten μl of 100 mg/ml arachadonic acid in acetone was applied to the left ear of each mouse. Ten μl of acetone was applied to the right ear as a control. At 90 minutes, the animals were sacrificed with $CO_2$ and the ear thickness was measured in triplicate using a constant pressure micrometer (Ames, accurate to 0.1 mm) and the average was recorded in millimeters. Percent swelling is calculated by taking the difference between the left ear thickness and the right ear thickness and dividing by the right ear thickness. Percent inhibition is calculated by taking the difference between the percent swelling of the peptide group and the percent swelling of the control group and dividing by the percent swelling of the control group.

TABLE 1

Effects of HEPP & Analogs on the Edematous Phase of an Arachadonic Acid—Induced Inflammatory Response

| Peptide | Dose (mg/kg) | Percent Inhibition |
| --- | --- | --- |
| Asp—Ser—Asp—Pro—Arg | 100 | 56 |
| Asp—D—Ser—Asp—Pro—Arg | 100 | 39 |
| Asp—D—Ser—Asp—Val—Arg | 100 | 70 |
| Asp—Ser—Glu—Pro—Arg | 100 | 30 |
| Glu—Ser—Asp—Pro—Arg | 100 | 9 |
| Asp—Ser—Asp—Pro—Lys | 100 | 17 |
| Ac—Asp—Ser—Asp—Pro—Arg | 100 | 18 |

The peptides of the invention must be purified to exhibit therapeutic activity. Generally, the peptides of the invention should be at least about 60% pure as measured by HPLC. Preferably, the peptides of the invention should be at least about 90% pure as measured by HPLC. Most preferably the peptides of the invention should be at least about 95% pure as measured by HPLC.

Other tests which can be used to check the activities of the peptides are described in Hess et al., J. Immunol. 130, 717–721 (1983) (human lymphocyte responses); Ishizaka et al., J. Immunol. 102, 884–892 (1969) (histamine release); Alkan, Eur. J. Immunol., 8, 112–118 (1978) (antigen-induced proliferation assay for mouse T lymphocytes); Starkebaum et al., J. Lab. Clin. Med., 98, 280–291 (1981) (in vitro chemiluminescence assay).

TABLE 2

INHIBITORY EFFECT OF ACTIVE SITE PEPTIDE ON HUMAN NATURAL KILLER (NK) CELL-INDUCED CYTOTOXICITY

| Peptide Used (μg/ml) | % cytotoxicity | % inhibition | % cytotoxicity | % inhibition | % cytotoxicity | % inhibition |
| --- | --- | --- | --- | --- | --- | --- |
| Media only | 29.4 | n.a. | 24.8 | n.a. | 14.5 | n.a |
| 100 equiv | 41.3 | n.a. | 30.2 | n.a. | 17.6 | n.a. |
| 50 equiv. | 44.8 | n.a. | 33.0 | n.a. | 19.3 | n.a. |
| 25 equiv. | 43.6 | n.a. | 32.8 | n.a. | 17.3 | n.a. |
| Average | | | | | | |
| Asp—Ala—Arg—His (100) | 24.5 | 43.3 | 16.4 | 48.7 | 10.5 | 42.0 |
| Asp—Ala—Arg—His (50) | 13.8 | 68.1 | 12.8 | 60.0 | 7.5 | 58.6 |
| Asp—Ala—Arg—His (25) | 19.3 | 55.3 | 12.9 | 59.7 | 6.8 | 62.4 |
| Pro—Asp—Ala—Arg (100) | 17.1 | 60.4 | 10.4 | 67.5 | 5.6 | 69.1 |
| Pro—Asp—Ala—Arg (50) | 23.1 | 46.5 | 15.5 | 51.6 | 10.3 | 43.1 |
| Pro—Asp—Ala—Arg (25) | 22.7 | 47.4 | 17.8 | 44.3 | 10.1 | 44.2 |
| Ala—Arg—His—Ser (100) | 21.8 | 49.5 | 18.5 | 42.2 | 10.6 | 41.4 |
| Ala—Arg—His—Ser (50) | 26.3 | 39.1 | 20.7 | 35.3 | 10.4 | 42.5 |
| Ala—Arg—His—Ser (25) | 24.8 | 42.6 | 19.4 | 39.4 | 12.5 | 30.9 |

1. To calculate percent inhibition, the average of the three dilutions of phosphate-buffered saline peptide diluent was used as the "control" for cytotoxicity. The 100, 50, and 25 equiv. notation indicates that the phosphate-buffered saline used to determine "control" values was diluted with culture medium in a manner identical to the dilutions used to produce the three peptide concentrations.
2. N K effector cells were human mononuclear cells freshly isolated by ficoll-metronidazole gradient. Targets were K562 human erythroleukemia cells.

Table 2 demonstrates representative immunomodulatory activity of different subject peptides, viz., Asp-Ala-Arg-His, Pro-Asp-Ala-Arg, and Ala-Arg-His-Ser, when incubated with normal human mononuclear cells (lymphocytes and monocytes) separated by ficoll-metronidazole gradient. The cells were exposed to the peptide (final concentration=100 micrograms/ml) for 1 hour and then used in a natural killer (NK) cell assay which measures the ability of NK lymphocytes to kill certain living cell "targets" (Seaman, W. E., et al., *J. Clin. Invest.* 67:1324, 1981).

The target cells used were a human erythroleukemia cell line K562 which has molecular structures recognized by NK cells. The K562 targets were prepared by incubating them with the radioactive isotope chromium 51 which is incorporated within the cells. The cells were then washed to remove externally adherent chromium 51 and 20,000 K562 cells were added to 400,000, 200,000 and 100,000 mononuclear cells to provide NK killer-to-target ratio of 20 to 1, 10 to 1, and 5 to 1, respectively, in a final volume of 200 microliters. After a 3-hour incubation at 37° C. in a 5% $CO_2$ atmosphere, the amount of chromium 51 in the supernatent (released from dead target cells) was counted to quantitate the amount of NK killing activity. The killing activity of peptide-treated cells was compared to non-peptide treated cells to assess the peptide's effect on NK killing activity. Table 2 demonstrates that one of the subject peptides inhibited, in a dose-dependent manner, NK killing activity. Because NK cells are thought to significantly contribute to rejection of transplanted bone marrow (Herberman, R. B., *Mol. Immunol.* 19:1313, 1982) and may contribute to rejection of transplanted hearts (Marboe, C. C. et al., *Clin. Immunol. Immunopath.* 27:141, 1983), the subject peptides and their analogs may prove useful in reducing or preventing the rejection phenomenon.

In the practice of the method of the present invention, an effective amount of polypeptide or derivative thereof, or a pharmaceutical composition containing same, as defined above, is administered via any of the usual and acceptable methods known in the art, either singly or in combination with another compound or compounds of the present invention or other pharmaceutical agents such as antihistamines, corticosteroids, and the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as discussed in more detail hereinafter. The administration can be conducted in single unit dosage form with continuous therapy or in single dose therapy ad libitum.

In one preferred embodiment, the method of the present invention is practiced when the relief of symptoms is specifically required or perhaps imminent; in another preferred embodiment, the method hereof is effectively practiced as continuous or prophylactic treatment.

In view of the foregoing as well as in consideration of the degree of severity of the condition being treated, age of subject, and so forth, all of which factors being determinable by routine experimentation by one skilled in the art, the effective dosage in accordance herewith can vary over a wide range. Since individual subjects vary in their Fc receptor content, an effective systemic dosage in accordance herewith can best be described as between $2 \times 10^3$ and $2 \times 10^6$ times the Fc receptor content, on a molar scale. For an average subject this would be between about 0.5 and 500 mg/kg/day, depending upon the potency of the compound. Of course, for localized treatment, e.g., of the respiratory system, proportionately less material will be required. Appropriate local dosages for use in inhibiting arachadonic acid-induced inflammation may be ascertained using standard animal and clinical testing methods.

Useful pharmaceutical carriers for the preparation of the compositions hereof, can be solids, liquids or gases; thus, the compositions can take the form of tablets, pills, capsules, powders, enterically coated or other protected formulations (such as by binding on ion exchange resins or other carriers, or packaging in lipid protein vesicles or adding additional terminal amino acids or replacing a terminal amino acid in the L-form with one in the D-form), sustained release formulations solutions (e.g., opthalmic drops), suspensions, elixirs, aerosols, and the like. The carrier can be selected from the various oils including those of petroleum, animal, vegetable or synthetic origin, for example, peanut oil, soybean oil, mineral oil, sesame oil, and the like. Water, saline, aqueous dextrose, and glycols are preferred liquid carriers, particularly (when isotonic) for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, an the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulation are described in "Remington's Pharmaceutical Sciences" by E. W. Martin. Such compositions will, in any event, contain an effective amount of the active compound together with a suitable amount of carrier so as to prepare the proper dosage form for proper administration to the host.

To be effective for the prevention of treatment of the allergic reaction it is important that the therapeutic agents be relatively non-toxic, non antigenic and non-irritating at the levels in actual use.

SYNTHESIS OF PEPTIDES

Petides of this invention were synthesized by the solid phase peptide synthesis (or Merrifield) method. This established and widely used method, including the experimental procedures, is described in the following references:

Merrifield, J. Am. Chem. Soc., 85, 2149–2154 (1963).
Meienhofer in "Hormonal Proteins and Peptides," ed. C. H. Li, Vol. 2 (Academic Press, 1973), pp. 48–267.
Barany and Merrifield in "The Peptides," eds. E. Gross and F. Meinenhofer, Vol. 2 (Academic Press, 1980), pp. 3–285.

A preferred method for synthesizing the peptides of the present invention is well known to those skilled in the art and is set forth in detail in the article entitled "Synthesis of a Tetrapeptide" by R. B. Merrifield, Journal of the American Chemical Society (Vol. 85, pp. 2–2154, 1963) as well as Meienhofer, cited above.

In this preferred method a peptide of any desired length and of any desired sequence is produced through the stepwise addition of amino acids to a growing peptide chain which is bound by a covalent bond to a solid resin particle.

In the preferred application of this method the C-terminal end of the growing peptide chain is covalently bound to a resin particle and amino acids having protected amino groups are added in the stepwise manner indicated above. A preferred amino protecting group is the t-BOC group, which is stable to the condensation conditions and yet is readily removable without destruction of the peptide bonds or racemization of chiral centers in the peptide chain. At the end of the procedure the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acid conditions.

The cleaved peptides are isolated and purified by means well known in the art such as, for example, lyophilization followed by either exclusion or partition chromatography on polysaccharide gel media such as Sephadex G-25, or countercurrent distribution. The composition of the final peptide may be confirmed by amino acid analysis after degradation of the peptide by standard means.

Salts of carboxyl groups of the peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the polypeptides may be prepared by contacting the polypeptide with one or more equivalents of the desired inorganic or organic acid, such as, for example, hydrochloric acid.

Esters of carboxyl groups of the polypeptides may be prepared by any of the usual means known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus the C-terminal end of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

The coupling, deprotection/cleavage reactions and preparation of derivatives of the subject polypeptides are suitably carried out at temperatures between about $-10°$ and $+50°$ C., most preferably about $20°-25°$ C. The exact temperature for any particular reaction will of course be dependent upon the substrates, reagents, solvents and so forth, all being well within the skill of the practitioner. Illustrative reaction conditions for these processes may be gleaned from the examples.

The peptides of this invention may also be synthesized using any techniques that are known to those in the peptide art, for example, those described in Houben-Weyl, Methoden Der Organischen Chemie, Vol. 15-II, pg. 1-806 (1974), Georg-Thieme-Verlag, Stuttgart; or in U.S. Pat. No. 4,161,522 and the references cited therein.

It is, furthermore, possible to prepare the present peptides using techniques of genetic engineering. Moreover, it is possible to prepare such peptides by cleavage, particularly by specific enzymatic cleavage of longer peptides which, in turn, may have been prepared by means of genetic engineering.

Rf-values were determined by thin layer chromatography (TLC) on cellulose using n-butanol:pyridine:acetic acid:water (15:10:3:12), and Rf*-values of silica using n-butanol:ethyl acetate:acetic acid:water (1:1:1:1), unless otherwise noted. Except by TLC, the purity of the peptides prepared was proven by high pressure liquid chromatography, amino acid analysis and paper electrophoresis.

The following examples are given to enable those skilled in the art to more fully understand and practice the present invention. They should not be construed as a limitation upon the scope of the invention, but merely as being illustrative and representative thereof.

EXAMPLE 1

Preparation of the pentapeptide Asp-Thr-Asp-Pro-Arg

Step 1

BOC-Pro-OH (1.1 mole) and N-methylmorpholine (1.1 mole) were dissolved in dry tetrahydrofuran (2-3 liters) and the solution cooled in a dry ice-acetone bath to $-20°$ C. Isobutyl chloroformate (1.1 mole) was added with vigorous stirring, keeping the temperature below $-10°$ C. After the addition of isobutyl chloroformate was complete, the mixture was stirred for five minutes at $-15$ C. A precooled solution ($-5°$ C.) of Arg($NO_2$)-OBzl (1 mole) and N-methylmorpholine (2.1 mole) in a mixture of tetrahydrofuran (500-1000 ml) and dimethylformamide (500-1000 ml) was then added to the mixed anhydride solution, with stirring. After stirring for 6-10 hours, the reaction mixture was evaporated under vacuum below 35° C. The residue was dissolved in ethyl acetate (6000 ml) and the solution washed successively with 1N hydrochloric acid (5×1000 ml), distilled water (5×1000 ml), 5% sodium bicarbonate (5×1000 ml), and distilled water (5×1000 ml). The organic layer was dried over anhydrous sodium sulfate or magnesium sulfate (200-500 g). The solvent was evaporated to about 500 ml and then triturated with anhydrous ether (2-5 liters) and hexane (2-5 liters). The resulting solid was filtered and washed with ether (2-5 liters). Yield of the intermediate, BOC-Pro-Arg($NO_2$)-OBzl, was about 60-90%.

Step 2

BOC-Pro-Arg($NO_2$)-OBzl was dissolved in methylene chloride (1-2 liters) and then added to cold (0° C.) trifluoroacetic acid (1-2 liters). After 30 minutes, the trifluoroacetic acid was evaporated under vacuum. The residue was triturated with anhydrous ether (4-10 liters) and the supernatent decanted. The trituration was repeated twice more with ether (3-4 liters). The product, H-Pro-Arg($NO_2$)-Bzl, was filtered and washed with ether (2×3 liters). The yield was 80-95%.

Step 3

Steps 2 and 1 were repeated using amino acid derivatives BOC-Asp(OBzl)-OH, BOC-Thr(Bzl)-OH and BOC-Asp(OBzl)-OH, consecutively. The reaction products were:
BOC-Asp(OBzl)-Pro-Arg($NO_2$)-OBzl,
BOC-Thr(Bzl)-Asp(OBzl)-Pro-Arg($NO_2$)-OBzl, and BOC-Asp(OBzl)-Thr(Bzl)-Asp(OBzl)-Pro-Arg(NO$_2$)-OBzl.

Step 4

The completely protected pentapeptide resulting from completion of Step 3, BOC-Asp(OBzl)-Thr(Bzl)-Asp(OBzl)-Pro-Arg(NO$_2$)-OBzl, was dissolved in a mixture of acetic acid (500 ml), water (500 ml), and methanol (3–5 liters). Palladium 10% on activated carbon (100–200 g) was added to the solution and hydrogen gas passed through the mixture for 20–40 hours. The catalyst was removed by filtration and the filtrate evaporated to dryness. The residue was triturated with ether (3–4 liters), and the resulting solid filtered to produce BOC-Asp-Thr-Asp-Pro-Arg. The yield was about 40–60%.

Step 5

The pentapeptide resulting from Step 4 was next deprotected using trifluoroacetic acid as described in Step 2 to yield Asp-Thr-Asp-Pro-Arg. The yield was about 60–80%.

Step 6

The pentapeptide of Step 5 was purified over a DEAE Sephadex A-25 column (4L) using ammonium bicarbonate gradients. The fractions obtained from this chromatography were monitored by thin layer chromatography (TLC) over silica gel plates using the solvent system n-butanol:acetic acid:ethyl acetate:water (1:1:1:1, v/v) and by reverse phase high performance liquid chromatography (HPLC) over a C18 column. Fractions containing pure material were pooled and the product was isolated by lyophilization. Overall yield of this purified material, Asp-Thr-Asp-Pro-Arg, was approximately 20%.

EXAMPLE 2

Preparation of Asp-Ser-Asp-Val-Arg

This material was prepared and purified following the procedure described in Example 1, substituting consecutively the following amino acid derivatives for those used in Steps 1–3:
H-Arg(NO$_2$)-OBzl,
BOC-Val-OH,
BOC-Asp(OBzl)-OH,
BOC-Ser-(Bzl)-OH, and
BOC-Asp(OBzl)-OH.
The overall yield of the product peptide, Asp-Ser-Asp-Pro-Arg, was about 18%.

EXAMPLE 3

Preparation of Asp-Ser-Asp-Ala-Arg

This peptide was prepared and purified following the procedure described in Example 1, substituting consecutively the following amino acid derivatives for those used in Steps 1–3:
H-Arg(NO$_2$)-OBzl,
BOC-Ala-OH,
BOC-Asp(OBzl)-OH,
BOC-Ser(Bzl)-OH, and
BOC-Asp(OBzl)-OH.
The overall yield of the product peptide, Asp-Ser-Asp-Ala-Arg, was about 25%.

EXAMPLE 4

Preparation of Asp-Ser-Glu-Pro-Arg

This material was prepared and purified following the procedure described in Example 1, substituting consecutively the following amino acid derivatives for those used in Steps 1–3:
H-Arg(NO$_2$)-OBzl,
BOC-Pro-OH,
BOC-Glu(OBzl)-OH,
BOC-Ser(Bzl)-OH, and
BOC-Asp(OBzl)-OH.
The overall yield of the product peptide was about 20%.

Each of the peptides of the present invention may be prepared by an analogous procedure by the stepwise addition of the desired amino acid to the growing peptide chain which is bound by a covalent bond to the solid resin.

EXAMPLE 5

Purification of Ac-Gln-Pro-Glu-Asn

After HF cleavage, the crude material (400 mg) was applied to purification by CCD using the solvent system n-butanol: acetic acid: water in a 4:1:5 ratio. After 250 transfers, fractions 33–37 were pooled to give 53 mg of the pure product. This was found to be pure by thin layer chromatography (solvent system n-BuOH: pyridine: acetic acid: water, 1:1:1:1) high pressure liquid chromatography, paper electrophoresis and amino acid analysis. Rf 0.37.

EXAMPLE 6

Purification of Thr-Arg-Ala-Glu

The HF cleaved crude Thr-Arg-Ala-Glu (300 mg) was purified by a G 25 partition column using n-butanol:acetic acid:water (4:1:5) upper layer as the eluent to afford partially purified Thr-Arg-Ala-Glu (163 mg). This peptide was further purified by reversed phase liquid chromatography (C-18, 40 micron) using 0.1% acetic acid as the eluting solvent to afford pure Thr-Arg-Ala-Glu (54 mg). Rf 0.31.

EXAMPLE 7

Purification of Glu-Lys-Gln-Arg

Crude peptide was purified by counter-current distribution using n-butanol: acetic acid: water (4:1:5) system to afford Glu-Lys-Gln-Arg. This peptide was purified by reversed phase liquid chromatography (C-18, 40 micron) using 0.1% acetic acid to give the pure Glu-Lys-Gln-Arg. Rf 0.06.

EXAMPLE 8

Purification of Asp-Lys-Ser-Arg

The dry peptide resin (7.3 g) was placed into the reaction vessel of the HF cleavage apparatus and was treated with 60 ml of liquid HF and 8 ml anisole at 0° C. for 60 minutes. After extraction and lyophilization, approximately 1 g crude peptide was isolated.

The entire batch was purified by CCD (counter-current distribution) using the solvent system n-butanol:acetic acid:water in in 1:5 ratio. After 220 transfers, fractions 65–110 were pooled to give approximately 1 g of product. The product was purified by liquid chromatography using a cation exchange column and partition columns. The purified product was confirmed by amino acid analysis. Rf 0.11.

EXAMPLE 9

(A) A solution of the tetrapeptide Asp-Lys-Ser-Arg in water is treated with 1 equivalent of 0.1N NaOH and the monosodium salt of the peptide is isolated by lyophilisation. By the use of 2 equivalents of 0.1N NaOH the corresponding disodium salt is obtained.

Similarly, this peptide may be converted to other metallic salts, e.g., K, Li, Ba, Mg, ammonium, Fe(II), Zn, Mn(II) and Al salts by substitution of the appropriate base.

(B) The addition of 1 equivalent of triethylamine to the solution of Thr-Ser-Gly-Pro-Arg in methanol, followed by careful evaporation of the solvent, yields the monotriethylammonium salt. Similarly this pentapeptide may be converted to other amine salts using, e.g., trimethylamine, tri(n-propyl)amine, dicyclohexylamine, (dimethylamino)ethanol, (diethylamino)ethanol, triethanolamine, tris(hydroxymethyl)aminomethane, arginine, lysine, histidine, N-ethylpiperidine, hydrabamine, choline, betaine, ethylenediamine, glucosamine, methylglucamine, theobromine, purine, piperazine, piperidine, caffeine and procaine salts, by substitution of the appropriate amine.

(C) In a similar manner, the other peptides of Examples 1 to 8 may be converted to their corresponding metallic and amine salts.

EXAMPLE 10

Neutralization of a solution of Thr-Ser-Gly-Pro-Arg in either water or methanol with 1 or 2 equivalents of hydrochloric acid gives the mono- and dihydrochloride salts respectively. The salts are isolated either by lyophilization of an aqueous solution or by precipitation with ether from a methanolic solution.

Similarly, this peptide may be converted to other acid addition salts, e.g., the hydrobromide, sulfate, phosphate, nitrate, acetate, oxalate, tartrate, succinate, maleate, fumarate, gluconate, citrate, malate, ascorbate, and benzoate salts, by substituting the appropriate acid for hydrogen chloride.

In a similar manner, the other peptides of Examples 1 to 8 may be converted to their corresponding acid addition salts.

EXAMPLE 11

Asp-Lys-Ser-Arg-OMe is treated with a saturated solution of ammonia in methanol at room temperature for 2 days. The solvent is removed in vacuo to afford Asp-Lys-Ser-Arg-NH$_2$.

Utilizing similar procedures, the corresponding amides of the other peptides of Examples 1 to 12 may be prepared.

EXAMPLE 12

A mixture of 500 mg of Gln-Pro-Glu-Asn, 0.7 ml of acetyl choride, 0.5 ml of pyridine and 10 ml of tetrahydrofuran is kept at 20° for 12 hours. The mixture is evaporated, the residue is purified by means of TLC to yield Ac-Gln-Pro-Glu-Asn.

EXAMPLE 13

In analogy to Example 12, Asp-Lys-Ser-Arg yields an N,N,O-triacetyl derivative. Utilizing similar procedures, the corresponding acyl derivatives, particularly N-terminal acetyl derivatives, of the peptides of Examples 1 to 8 may be prepared.

EXAMPLE 14

The following illustrate typical pharmaceutical compositions of the compounds hereof, exemplified by Thr-Ser-Gly-Pro-Arg:

EXAMPLE 14 A: Aerosol Formulation (per dose)

| | |
|---|---|
| Thr—Ser—Gly—Pro—Arg | 10 mg. |
| Sodium chloride | 6.9 mg. |
| Sodium monobasic phosphate monohydrate | 5.8 mg |
| Water to make | 1.0 ml |

EXAMPLE 14 B: Injectable Formulation (per dose)

| | |
|---|---|
| Thr—Ser—Gly—Pro—Arg | 10 mg. |
| Sodium chloride | 6.9 mg. |
| Sodium monobasic phosphate monohydrate | 5.8 mg |
| Methylparaben | 0.25 mg |
| Propylparaben | 0.14 mg |
| Water to make | 1.0 ml. |

EXAMPLE 14 C: Dry Powder Formulation for Inhalation

| | |
|---|---|
| Thr—Ser—Gly—Pro—Arg | 10 mg. |
| Lactose | 30 mg. |

EXAMPLE 15

In analogy to Example 1, the following peptides were prepared (N-acyl derivatives being prepared by replacing the terminal t-BOC-amino acid with the appropriate N-acylamino acid, e.g. N-acetyl glutamine (Ac-Gln)):
Leu-Asp-Gly-Lys, Rf 0.41
Leu-His-Gln-Asn, Rf 0.34
Thr-Val-Leu-His-Gln-Asn-Trp-Leu-Asp-Gly-Lys-Glu, Rf 0.58
Thr-Val-Leu-His Gln-Asn-Trp-Leu-Asp-Gly-Lys-Glu-Tyr, Rf 0.66 (on silica)
Thr-Val-Leu-His-Gln-Asn-Trp-Leu-Asp-Gly-Lys-Glu-Tyr-Lys, Rf 0.63
Thr-Val-Leu-His-Gln-Asn-Ala-Leu-Asp-Gly-Lys, Rf 0.55
Lys-Thr-lle-Ser-Lys-Ala-Lys-Gly-Gln-Pro-Arg, Rf 0.19
Thr-lle-Ser-Lys-Ala-Lys-Gly-Gln-Pro-Arg, Rf 0.28
Ser-Arg-Glu-Glu, Rf* 0.29
Asp-Lys-Ser-Arg-Trp-Gln-Gln-Gly-Asn, Rf 0.07 (on silica)
Tyr-Ser-Lys-Leu-Thr-Val-Asp-Lys-Ser-Arg, Rf 0.11
Ac-Gln-Gln-Gly-Asn, Rf 0.52
Ser-Asn-Asp-Gly-Glu-Pro-Glu-Asn-Tyr, Rf 0.33
Ser-Asn-Gly-Gln-Pro-Glu-Asn-Tyr, Rf 0.29
Asn-Gly-Gln-Pro, Rf 0.22
Gly-Gln-Pro-Glu-Asn, Rf* 0.19
Gln-Pro-Glu-Asn-Asn, Rf* 0.28
Ac-Gln-Pro-Glu-Asn-Asn-Tyr, Rf 0.53
Ac-Gln-Pro-Glu-Asn-Asn-Tyr-Lys, Rf 0.45
Gly-Gln-Pro-Glu-Asn-Asn, Rf 0.24 (on silica)
Ac-Glu-Pro-Glu-Asn-Asn, Rf* 0.35
Ac-Glu-Pro-Glu-Asp-Asn, Rf* 0.44

Ac-Gln-Pro-Glu-Asp-Asn, Rf 0.40
His-Asn-His-Tyr, Rf* 0.24
Glu-Ala-Leu-His-Asn-His-Tyr, Rf* 0.21
Thr-Lys-Thr-Ser-Gly-Pro-Arg, Rf 0.23
Thr-Ser-Gly-Pro-Arg, Rf 0.26
Gly-Thr-Arg-Asp Rf* 0.17
Thr-Gln-Pro-Arg, Rf* 0.17
Thr-Thr-Gln-Pro-Arg, Rf 0.30
Ala-Arg-His-Ser, Rf 0.26
Asp-Ala-Arg-His, Rf 0.14
Pro-Asp-Ala-Arg, Rf 0.20
Ac-Gln-Leu-Pro-Asp-Ala-Arg, Rf 0.53
Glu-Val-Gln-Leu-Pro-Asp-Ala-Arg, Rf 0.48
His-Asn-Glu-Val-Gln-Leu-Pro-Asp-Ala-Arg-His, Rf 0.32
Pro-Asp-Ala-Arg-His-Ser-Thr, Rf 0.31
Pro-Asp-Ala-Arg-His-Ser-Thr-Thr-Gln-Pro-Arg, Rf 0.28
Thr-Arg-Ala-Glu-Trp-Gln-Glu-Lys-Asp, Rf* 0.10
Glu-Gln-Lys-Asp, Rf 0.12
Thr-Arg-Ala-Glu-Ala-Glu-Gln-Lys-Asp, Rf 0.14
Arg-Ala-Val-His-Glu-Ala-Ala-Ser-Pro-Ser-Gln-Thr-Val, Rf 0.13
Asp-Lys-Ser-Lys, Rf 0.08.

It is understood that various other modifications will be apparent to and can readily be made by those skilled in the art without departing from the scope and spirit of this invention. Accordingly, it is not intended that the scope of the claims appended hereto be limited to the description as set forth above, but rather that the claims be construed as encompassing all the features of patentable novelty which reside in the present invention, including all features which would be treated as equivalents thereof by those skilled in the art to which this invention pertains.

What is claimed is:

1. An anti-inflammatory peptide having an amino acid sequence A-B-C-D-E wherein
   A is Asp or Glu;
   B is Ser, D-Ser, Thr, Ala, Gly, or Sarcosine;
   C is Asp, Glu, Asn, or Gln;
   D is Pro, Val, Ala, Leu, or Ile; and
   E is Arg, Lys, or Orn
and pharmaceutically acceptable salts thereof, provided that
   Asp-Ser-Glu-Pro-Arg,
   Asp-Ser-Asp-Pro-Arg,
   Asp-Ser-Asn-Pro-Arg, and
   Asp-Thr-Glu-Ala-Arg
are excluded.

2. A method of reducing an inflammatory response in a mammal, comprising administering an effective amount of a peptide having an amino acid sequence A-B-C-D-E wherein
   A is Asp or Glu;
   B is Ser, D-Ser, Thr, Ala, Gly, or Sarcosine;
   C is Asp, Glu, Asn, or Gln;
   D is Pro, Val, Ala, Leu, or Ile; and
   E is Arg, Lys, or Orn
and pharmaceutically acceptable salts thereof, provided that
   Asp-Ser-Asp-Pro-Arg,
   Asp-Ser-Asn-Pro-Arg, and
   Asp-Thr-Glu-Ala-Arg
are excluded.

3. A method of blocking immunoglobulin binding to basophil Fc receptors, comprising administering an effective amount to block immunoglobulin binding to basophil Fc receptors of a peptide having an amino acid sequence A-B-C-D-E wherein
   A is Asp or Glu;
   B is Ser, D-Ser, Thr, Ala, Gly, or Sarcosine;
   C is Asp, Glu, Asn, or Gln;
   D is Pro, Val, Ala, Leu, or Ile; and
   E is Arg, Lys, or Orn
and pharmaceutically acceptable salts thereof, provided that
   Asp-Ser-Asp-Pro-Arg,
   Asp-Ser-Asn-Pro-Arg, and
   Asp-Thr-Glu-Ala-Arg
are excluded.

4. A method of blocking immune complex binding to immunoglobulin Fc receptors, comprising administering an effective amount to reduce immune complex mediated inflammation or tissue destruction of a peptide having an amino acid sequence A-B-C-D-E wherein
   A is Asp or Glu;
   B is Ser, D-Ser, Thr, Ala, Gly, or Sarcosine;
   C is Asp, Glu, Asn, or Gln;
   D is Pro, Val, Ala, Leu, or Ile; and
   E is Arg, Lys, or Orn
and pharmaceutically acceptable salts thereof, provided that
   Asp-Ser-Asp-Pro-Arg,
   Asp-Ser-Asn-Pro-Arg, and
   Asp-Thr-Glu-Ala-Arg
are excluded.

5. An anti-inflammatory peptide according to claim 1 wherein A is Asp.

6. An anti-inflammatory peptide according to claim 1 wherein B is Ser.

7. An anti-inflammatory peptide according to claim 1 wherein C is Asp.

8. An anti-inflammatory peptide according to claim 1 wherein D is Pro.

9. An anti-inflammatory peptide according to claim 1 wherein E is Arg.

10. An anti-inflammatory peptide according to claim 1 wherein A is Asp and B is Ser.

11. An anti-inflammatory peptide according to claim 1 wherein A is Asp and B is D-Ser.

12. An anti-inflammatory peptide according to claim 1 wherein A is Asp and C is Asp.

13. An anti-inflammatory peptide according to claim 1 wherein A is Asp and D is Pro.

14. An anti-inflammatory peptide according to claim 1 wherein A is Asp and E is Arg.

15. An anti-inflammatory peptide according to claim 1 wherein B is Ser and C is Asp.

16. An anti-inflammatory peptide according to claim 1, wherein B is D-Ser and C is Asp.

17. An anti-inflammatory peptide according to claim 1 wherein B is Ser and D is Pro.

18. An anti-inflammatory peptide according to claim 1, wherein B is D-Ser and D is Pro.

19. An anti-inflammatory peptide according to claim 1 wherein B is Ser and E is Arg.

20. An anti-inflammatory peptide according to claim 1 wherein C is Asp and D is Pro.

21. An anti-inflammatory peptide according to claim 1 wherein C is Asp and E is Arg.

22. An anti-inflammatory peptide according to claim 1 wherein D is Pro and E is Arg.

23. An anti-inflammatory peptide according to claim 1 wherein said peptide is selected from the group consisting of Glu-Ser-Asp-Pro-Arg,
Asp-Thr-Asp-Pro-Arg,
Glu-Thr-Asp-Pro-Arg,
Asp-Ala-Asp-Pro-Arg,
Glu-Ala-Asp-Pro-Arg,
Glu-Ser-Glu-Pro-Arg,
Asp-Thr-Glu-Pro-Arg,
Glu-Thr-Glu-Pro-Arg,
Asp-Ala-Glu-Pro-Arg,
Glu-Ala-Glu-Pro-Arg,
Asp-Ser-Asp-Val-Arg,
Glu-Ser-Asp-Val-Arg,
Asp-Thr-Asp-Val-Arg,
Glu-Thr-Asp-Val-Arg,
Asp-Ala-Asp-Val-Arg,
Glu-Ala-Asp-Val-Arg,
Asp-Ser-Glu-Val-Arg,
Glu-Ser-Glu-Val-Arg,
Asp-Thr-Glu-Val-Arg,
Glu-Thr-Glu-Val-Arg,
Asp-Ala-Glu-Val-Arg,
Glu-Ala-Glu-Val-Arg,
Asp-Ser-Asp-Ala-Arg,
Glu-Ser-Asp-Ala-Arg,
Asp-Thr-Asp-Ala-Arg,
Glu-Thr-Asp-Ala-Arg,
Asp-Ala-Asp-Ala-Arg,
Glu-Ala-Asp-Ala-Arg,
Asp-Ser-Glu-Ala-Arg,
Glu-Ser-Glu-Ala-Arg,
Asp-Thr-Glu-Ala-Arg,
Glu-Thr-Glu-Ala-Arg,
Asp-Ala-Glu-Ala-Arg,
Glu-Ala-Glu-Ala-Arg,
Asp-Ser-Asp-Pro-Lys,
Glu-Ser-Asp-Pro-Lys,
Asp-Thr-Asp-Pro-Lys,
Glu-Thr-Asp-Pro-Lys,
Asp-Ala-Asp-Pro-Lys,
Glu-Ala-Asp-Pro-Lys,
Asp-Ser-Glu-Pro-Lys,
Glu-Ser-Glu-Pro-Lys,
Asp-Thr-Glu-Pro-Lys,
Glu-Thr-Glu-Pro-Lys,
Asp-Ala-Glu-Pro-Lys,
Glu-Ala-Glu-Pro-Lys,
Asp-Ser-Asp-Val-Lys,
Glu-Ser-Asp-Val-Lys,
Asp-Thr-Asp-Val-Lys,
Glu-Thr-Asp-Val-Lys,
Asp-Ala-Asp-Val-Lys,
Glu-Ala-Asp-Val-Lys,
Asp-Ser-Glu-Val-Lys,
Glu-Ser-Glu-Val-Lys,
Asp-Thr-Glu-Val-Lys,
Glu-Thr-Glu-Val-Lys,
Asp-Ala-Glu-Val-Lys,
Glu-Ala-Glu-Val-Lys,
Asp-Ser-Asp-Ala-Lys,
Glu-Ser-Asp-Ala-Lys,
Asp-Thr-Asp-Ala-Lys,
Glu-Thr-Asp-Ala-Lys,
Asp-Ala-Asp-Ala-Lys,
Glu-Ala-Asp-Ala-Lys,
Asp-Ser-Glu-Ala-Lys,
Glu-Ser-Glu-Ala-Lys,
Asp-Thr-Glu-Ala-Lys,
Glu-Thr-Glu-Ala-Lys,
Asp-Ala-Glu-Ala-Lys, and
Glu-Ala-Glu-Ala-Lys.

24. An anti-inflammatory peptide according to claim 1, wherein said peptide is selected from the group consisting of
Asp-D-Ser-Asp-Pro-Arg
Glu-D-Ser-Asp-Pro-Arg
Asp-D-Ser-Glu-Pro-Arg
Glu-D-Ser-Glu-Pro-Arg
Asp-D-Ser-Asp-Val-Arg
Glu-D-Ser-Asp-Val-Arg
Asp-D-Ser-Glu-Val-Arg
Glu-D-Ser-Glu-Val-Arg
Asp-D-Ser-Asp-Ala-Arg
Glu-D-Ser-Asp-Ala-Arg
Asp-D-Ser-Glu-Ala-Arg
Glu-D-Ser-Glu-Ala-Arg
Asp-D-Ser-Asp-Pro-Lys
Glu-D-Ser-Asp-Pro-Lys
Asp-D-Ser-Glu-Pro-Lys
Glu-D-Ser-Glu-Pro-Lys
Asp-D-Ser-Asp-Val-Lys
Glu-D-Ser-Asp-Val-Lys
Asp-D-Ser-Glu-Val-Lys
Glu-D-Ser-Glu-Val-Lys
Asp-D-Ser-Asp-Ala-Lys
Glu-D-Ser-Asp-Ala-Lys
Asp-D-Ser-Glu-Ala-Lys
Glu-D-Ser-Glu-Ala-Lys.

25. An anti-inflammatory peptide according to claim 1 wherein said peptide is an amino-terminal acetyl derivative of the form
Ac-A-B-C-D-E.

* * * * *